United States Patent
Niazi et al.

(10) Patent No.: US 12,416,635 B2
(45) Date of Patent: *Sep. 16, 2025

(54) LIVE CELL IMAGING SYSTEMS AND METHODS TO VALIDATE TRIGGERING OF IMMUNE RESPONSE

(71) Applicants: NantBio, Inc., Culver City, CA (US); Nant Holdings IP, LLC, Culver City, CA (US)

(72) Inventors: Kayvan Niazi, Culver City, CA (US); Shahrooz Rabizadeh, Agoura Hills, CA (US); Nicholas J Witchey, Culver City, CA (US)

(73) Assignees: NantBio, Inc., Culver City, CA (US); Nant Holdings IP, LLC, Culver City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/933,033

(22) Filed: Sep. 16, 2022

(65) Prior Publication Data

US 2023/0011700 A1 Jan. 12, 2023

Related U.S. Application Data

(63) Continuation of application No. 16/470,072, filed as application No. PCT/US2017/066898 on Dec. 17, 2017, now Pat. No. 11,480,572.

(60) Provisional application No. 62/435,520, filed on Dec. 16, 2016.

(51) Int. Cl.
| | | |
|---|---|---|
| *G01N 33/574* | (2006.01) | |
| *G01B 9/02* | (2022.01) | |
| *G01B 11/06* | (2006.01) | |
| *G01N 33/50* | (2006.01) | |

(52) U.S. Cl.
CPC ............. *G01N 33/574* (2013.01); *G01B 9/02* (2013.01); *G01B 11/06* (2013.01); *G01N 33/502* (2013.01)

(58) Field of Classification Search
CPC ......... G01N 33/574; G01B 9/02; G01B 11/06
See application file for complete search history.

(56) References Cited

U.S. PATENT DOCUMENTS

| | | |
|---|---|---|
| 2010/0284016 A1 | 11/2010 | Teitell et al. |
| 2014/0178865 A1 | 6/2014 | Reed et al. |
| 2016/0103118 A1 | 4/2016 | Teitell et al. |

FOREIGN PATENT DOCUMENTS

| | | |
|---|---|---|
| WO | 2015/103037 A2 | 7/2015 |
| WO | 2018/112449 A2 | 6/2018 |

OTHER PUBLICATIONS

Zangle et al., PLoS One 8(7): e68916 (2013).*
Chun et al., Analyst., 137(23): 5495-5498 (2012).*
Bougherara, Frontiers in Immunology, 2015, vol. 6, Article 500, pp. 1-12.*
Mir et al., "Highly Sensitive Quantitative Imaging for Monitoring Single Cancer Cell Growth Kinetics and Drug Response", PLOS One, Feb. 18, 2014, https://doi.org/10.1371/journal.pone.0089000, 9 pages.
Reed et al., "Rapid, Massively Parallel Single-Cell Drug Response Measurements via Live Cell Interferometry", Biophysical Journal, vol. 101, dated Sep. 2011, pp. 1025-1031.
Zangle et al., "Live-cell mass profiling: an emerging approach in quantitative biophysics", Nat Methods. Dec. 2014, 11(12): 1221-1228, dated Dec. 2014, pp. 1-20.
International Search Report and Written Opinion received for PCT Application Serial No. PCT/US17/66898, dated Oct. 31, 2018, 11 pages.
Zangle et al., "Quantifying Biomass Changes of Single CD8+ T Cells during Antigen Specific Cytotoxicity", Plos, vol. 8, No. 7, 8 pages, 2013.
International Preliminary Report on Patentability received for PCT Application Serial No. PCT/US17/66898, dated Jun. 27, 2019, 8 pages.
Snyder et al., "Genetic Basis for Clinical Responseto CTLA-4 Blockade in Melanoma", The New England Journal of Medicine, Dec. 4, 2014, vol. 371, No. 23, pp. 2189-20199.
Restriction Requirement received for U.S. Appl. No. 16/470,072 dated Nov. 23, 2021, 5 pages.
Non-Final Office Action received for U.S. Appl. No. 16/470,072 dated Feb. 22, 2022, 40 pages.
Bougherara et al., "Real-time imaging of resident T cells in human lung and ovarian carcinomas reveals how different tumor microenvironments control T lymphocyte migration", Frontiers in Immunology, Original Research, vol. 6, Article 500, Oct. 12, 2015, pp. 1-12.
Chun et al., "Rapidly Quantifying Drug Sensitivity of Dispersed and Clumped Breast Cancer Cells by Mass Profiling", National Institute of Health, vol. 137, No. 23, Dec. 7, 2012, pp. 1-8.
Notice of Allowance received for U.S. Appl. No. 16/470,072 dated Jun. 23, 2022, 15 pages.

* cited by examiner

*Primary Examiner* — Erin M. Bowers
(74) *Attorney, Agent, or Firm* — ROTHWELL, FIGG, ERNST & MANBECK, P.C.

(57) ABSTRACT

Systems and methods for predicting an immune response against a tumor in a patient having the tumor are provided. The relative mass or changes of mass of tumor cells or immune cell in the tumor can be ex vivo observed, and an immune status of the tumor can be determined based on the mass of tumor cells or immune cell. The immune status can provide a guidance to predict the immune response against the tumor in the patient.

13 Claims, No Drawings

LIVE CELL IMAGING SYSTEMS AND METHODS TO VALIDATE TRIGGERING OF IMMUNE RESPONSE

This application is a continuation of Ser. No. 16/470,072, filed Jun. 14, 2019, which is now allowed, which application is a national phase of PCT/US17/66898, filed Dec. 17, 2017, which claims priority to U.S. provisional application with the Ser. No. 62/435,520, filed Dec. 16, 2016. All of these applications are incorporated by reference herein.

FIELD OF THE INVENTION

The field of the invention is validation of a neoepitope-based therapy prior to use of a therapeutic composition in a patient.

BACKGROUND OF THE INVENTION

The background description includes information that may be useful in understanding the present invention. It is not an admission that any of the information provided herein is prior art or relevant to the presently claimed invention, or that any publication specifically or implicitly referenced is prior art.

All publications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Despite recent advances in the diagnosis and treatment of cancer, many types of cancers remain difficult to cure or drive into long term remission. Currently, one promising avenue of research is the individualized therapy of cancers. The concept of individualized therapy is based on the observation that each cancer, in each individual patient or subject, is in some ways unique. Thus, if the therapy is tailored to address or target the genetic elements and/or regulatory cellular pathway(s) altered or mis-regulated in a specific tumor, the prospects of a successful treatment against the tumor are likely to be enhanced. For example, recent development of various immunotherapies is targeted to specifically elicit immune response against cells exposing neoepitopes that are mostly patient-specific and tumor-specific. While the individualized immunotherapy seems promising to treat many tumors that could not be effectively treatable previously, the effectiveness of such individualized immunotherapy often unexpectedly vary due to numerous factors that can reduce the efficacy of the treatment. For example, inter alia, some tumor cells may not efficiently process and present neoepitope on the cell surfaces, which may lead to a failure of eliciting immune responses against the tumor cells. In addition, the patient's specific T-cell population may lack proper responsiveness, for example, due to checkpoint inhibitory signaling that is prevalent in tumor microenvironment, or due to a large fraction of M2 macrophages, regulatory T cells (Tregs), and/or myeloid-derived suppressor cells (MDSCs). Therefore, even where patient and tumor specific neoepitopes are selected or designed for proper MHC presentation, the effectiveness of the individual immunotherapy may vary depending on the tumor cell types and the tumor microenvironment.

Live cell interferometry (LCI) detects the live cells and provides rapid and real-time quantification of cell mass in cells, thus can be used for various assessment including cell mass changes upon changes during response to the drugs. For example, U.S. Patent Pub. No. 2014/0178865 discloses measurement of cell mass, or optical cell thickness of multiple myeloma cells upon tunicamycin treatment. In another example, U.S. Patent Pub. No. 2016/0103118 discloses identifying T cell receptors that respond to specific target cell antigens by detecting mass changes in T cells. However, none of those discloses use of LCI to predict whether a tumor cell or the tumor mass will be responsive to effective immunotherapy.

Thus, even though various compositions and methods of individualized immunotherapy are known in the art, evaluation of individual tumors for their suitability for individualized immunotherapy, especially using LCI, is largely unexplored. Consequently, there is still a need for systems and methods that help predict effectiveness of individualized immunotherapy in a patient.

SUMMARY OF THE INVENTION

The inventive subject matter is directed to various methods and systems of predicting an anticipated immune response to a tumor in a patient having the tumor, especially prior to an immunotherapeutic treatment to the patient, in which the immune status is determined by live cell interferometry (LCI) analysis of tumor cells and immune competent cells present in the tumor. In addition, the LCI analysis of the tumor cells and immune competent cells can be further extended to evaluate the effectiveness of the immunotherapeutic treatment.

Thus, in one especially preferred aspect of the inventive subject matter, the inventor contemplates a method of predicting an immune response against a tumor in a patient having the tumor. In this method, a tumor sample of the patient is obtained prior to immunotherapeutic treatment of the patient. Then, the mass of a tumor cell and/or the mass of an immune competent cell is determined in the tumor sample using live cell interferometry. Using the determined mass of a tumor cell and/or the mass of an immune competent cell, an immune status of the tumor sample can be further determined, and be used to predict the immune response against the tumor in the patient.

In further contemplated aspects, the step of determining the mass of the tumor and/or immune competent cell will include measuring changes over a period of time (e.g., several hours) in the mass of the tumor and/or the immune competent cell. Additionally or alternatively, the specific interaction between the tumor cell (isolated or in the tissue) and one or more types of immune competent cells can be determined, where the tumor cell is located proximally to the immune competent cell, by comparing the mass of the tumor cell or the immune competent cell with an average mass of other tumor cells or immune competent cells, respectively, in the tumor sample.

It is also contemplated that the methods presented herein may include a step of contacting the tumor sample with an immune stimulatory cytokine, a checkpoint inhibitor, and/or an immunotherapeutic agent (e.g., neoepitope peptide, nucleic acid encoding a neoepitope, etc.). Where desired, the immune competent cell may be an immune competent cell of the patient that was previously exposed to an immunotherapeutic agent.

In other aspects, the immune status may be determined to be hot when the mass of the tumor cell is substantially smaller than other tumor cells in the tumor sample, when the mass of the immune competent cell is substantially larger than other immune competent cells in the tumor sample, and/or when the mass of the immune competent cell is substantially larger than other immune competent cells in the tumor sample and when the mass of the tumor cell is substantially smaller than other tumor cells in the tumor sample where the tumor cell is proximal to the immune competent cell. An anticipated immune response may then be deemed positive when the immune status is determined to be hot. If the immune status is determined to be cold, it is contemplated that immunotherapeutic treatment may be modified or other alternative options for the immunotherapeutic treatment can be provided.

With respect to the tumor sample, it is contemplated that the tumor sample can be a fresh tumor biopsy from the patient or can be an artificial tumor that is generated from a tumor biopsy of the patient. The tumor sample can be further prepared as one or more acute tissue slices, cultured slices, or as a disassociated cell culture (using adherent or suspended cells, optionally from trypsinated tissue) placed on a dish, or any solid carrier or support. Optionally, the tumor cell and the immune competent cell in the tumor sample can be fixed after live cell interferometry (LCI) analysis for labeling the cells with one or more markers and identifying the cell types.

Various objects, features, aspects and advantages of the inventive subject matter will become more apparent from the following detailed description of preferred embodiments.

DETAILED DESCRIPTION

Most tumors present as a heterogeneous mass of various types of cells in addition to the tumor cells, and frequently include various immune cells, bone marrow-derived inflammatory cells, lymphocytes, fibroblasts, as well as an extracellular matrix and epithelial cells structuring surrounding blood vessels. Proliferation of tumor cells in the tumor microenvironment typically is closely related to the interaction of tumor cells and other cells surrounding the tumor cells. Especially, the dynamic interactions between the tumor cells and immune cells in the tumor environment often shift balances between a cytotoxic immune response to the tumor and immune-suppression in the tumor microenvironment such that the tumor cells are in a sensitive status or in a resistant status (e.g., primary resistance, adaptive immune resistance, acquired resistance, etc.) to a host (e.g., patient) immune response.

The inventors contemplate that the tumor cells in the immune-sensitive ("hot") status are likely to be susceptible to the immunotherapy and that the tumor cells in the immune-resistant ("cold") status are less likely to be susceptible to the immunotherapy. Viewed from a different perspective, the inventors contemplate that effectiveness of the immunotherapy can be predicted by determining the immune-sensitive or immune-resistant status of the tumor cells and/or tumor microenvironment. With that, the inventors have now discovered that the immune response of a patient against its tumor cells can be predicted substantially in real-time (e.g., within less than 24 hours, or within less than 12 hours, or within less than 6 hours from obtaining tumor cells/tissue) by observing and/or comparing the cell mass of tumor cells and/or immune competent cells within the tumor mass or tumor microenvironment. Advantageously, such methods will allow rapid commencement of immune therapy in a patient upon first biopsy or surgery (and may as such avoid chemotherapy that would otherwise potentially harm the immune system).

As used herein, the term "tumor" refers to, and is interchangeably used with one or more cancer cells, cancer tissues, malignant tumor cells, or malignant tumor tissue, that can be placed or found in one or more anatomical locations in a human body.

As used herein, the term "bind" refers to, and can be interchangeably used with a term "recognize" and/or "detect", an interaction between two molecules with a high affinity with a $K_D$ of equal or less than $10^{-6}$M, or equal or less than $10^{-7}$M. As used herein, the term "provide" or "providing" refers to and includes any acts of manufacturing, generating, placing, enabling to use, or making ready to use.

Most preferably, profiling of cell mass of tumor cells and/or immune competent cells can be performed using live cell interferometry (LCI), which can determine the cell mass of a plurality of adherent or non-adherent cells under the microscope almost simultaneously. As used herein, cell mass is measured using the optical thickness (density) of the cell and surrounding environment. Briefly, the optical thickness of a living cell in a sample can be compared with the optical thickness of the surrounding media (e.g., cell culture media, tissue culture media, intermediate buffer, etc.), which is measured by phase retardation of the light passing through each cell. The difference between those optical thicknesses is due to the interaction of light with cellular biomass, which is linearly proportional to the material density of a cell. The detailed method and algorithm of the measuring the cell mass using the LCI on a single cell scale is provided in Reed et al., *Biophysical Journal*, Volume 101, pp. 1025-1031 (September 2011), 102.3 (2012) and Zangle et al., *Nature Methods*, 11, 1221-1228 (2014), and in a multi-cell scale is provided in U.S. Patent Pub. No. 2014/0178865 to Reed, and U.S. Patent Pub. No. 2016/0103118 to Teitell, which are all incorporated by references in their entireties herein.

Optionally, the optical thickness of the cell can be compared and/or normalized with the physical thickness (e.g., height) of the cell. Any suitable methods of measuring the physical thickness of cells are contemplated, including, but not limited to measurement using optical phase microscope.

The inventors observed that immunologically active cytotoxic or cytolytic immune cells (e.g., active T cell, cytotoxic T cells, active NK cells, active NKT cells attacking cells upon recognition of the antigens or neoepitopes presented on the cells, etc.) increase their mass upon interacting with the cells presenting antigens or neoepitopes. Conversely, immunogenic cell (e.g., immune-sensitive tumor cells, tumor cells expressing antigens or neoepitopes) interacting with and being attacked by the immune cells (e.g., either cytolytic or cytotoxic attack, etc.) are likely to decrease their mass (e.g., due to apoptosis, necrosis, etc.). Therefore, viewed from a different perspective, decreased mass of the immune cells can be an indicator an of inactive or suppressed immune response or immune system in the tumor microenvironment, and an increased mass of tumor cells can be an indicative of proliferation of the tumor cells that overcome the immune response against the tumor cells in the tumor microenvironment.

Thus, in one especially preferred embodiment, an immune response against a tumor in a patient having the tumor can be predicted by determining the cell mass of a tumor cell and/or an immune competent cell in a tumor sample. Most typically, the tumor sample is obtained from the patient through a biopsy of the tumor tissue during the surgery or regular biopsy procedure. Preferably, the biopsy tumor tissue can be further processed for observation under the LCI and other types of microscopic analysis, if necessary. In one embodiment, the biopsy tumor tissue can be processed via manual and/or automated tissue slicing (e.g., using Leica Vibratome, etc.) under semi-sterile conditions, into acutely sliced tissues with a thickness of 100-500 μm, preferably 150-400 μm, and more preferably about 150-300 μm, and most preferably about 200-250 μm per each slice. The acutely sliced tumor tissue can be placed on a chamber for observation under the LCI and other types of microscope within 10 min, within 30 min, or within 1 hour after the slices are generated. Additionally, the acutely sliced tumor tissue can be moved to a chamber containing tissue culture media (e.g., Dulbecco's modified eagle media (DMEM)-based tissue culture media, Gibco® RPMI-1640-based media, etc.), for example, to be cultured in 37° C., 5% CO2 environment for at least 6 hours, at least 12 hours, at least 24 hours, at least 3 days, at least 7 days, before the observation under the LCI and other types of microscope.

Alternatively, the biopsy tumor tissue or the acutely sliced tumor tissue can be processed with enzymatic disassociation using one or more of trypsin, papain, elastase, hyaluronidase, collagenase, pronase and deoxyribonuclease, depending on the type, origination, or location of the tumor, and optionally in combination with mechanical and chemical disassociation tools (e.g., using cation chelators including EDTA and EGTA, etc.). For example, trypsin can be suitably used to disassociate tumor cells originated from brain, epidermis, kidney and lung, and papain can be suitably used to disassociate tumor cells originated from muscle. Once disassociated, the cells from the biopsy tumor tissue may be cultured and maintained in the cell culture medium for at least 6 hours, at least 12 hours, at least 24 hours, at least 3 days, at least 7 days, before thither observation under the LCI and other types of microscope.

In some embodiment, the entire biopsy tumor tissue or the tumor tissue slice can be used. In other embodiments, the biopsy tumor tissue or the tumor tissue slice can be further processed into (e.g., punched, etc.) smaller tissues pieces (e.g., less than 2 mm×2 mm, less than 1.5 mm×1.5 mm, less than 3 mm diameter, less than 2 mm diameter, etc.). In such embodiments, the inventors contemplate that the locations of the smaller tumor tissues can be mapped relative to the entire or at least a portion of the biopsy tissue to determine or identify any heterogeneity in immune-responsiveness status (e.g., immune-sensitive, immune-resistant status) among sub-regions of the tumor.

As it represents a tumor microenvironment, the biopsy tumor tissue is likely to include different types of cells including, but not limited to, tumor cells, immune cells, and epithelial cells (e.g., from the blood vessel surrounding the tumor, etc.). As used herein, immune cells refer any cells (cytotoxic or non-cytotoxic immune cells) in the immune system, including, but not limited to, B cells, T cells, cytotoxic T cells, natural killer (NK) cells, natural killer T (NKT) cells, macrophage, monocytes, and innate lymphoid cells. In addition, as used herein, immune competent cells refer any immune cell that has ability to elicit immune response following the exposure to an antigen. In some embodiments, the immune cells also include myeloid derived suppressor cells (MDSC) that mediate immune suppression in the tumor microenvironment. In order to mimic the tumor microenvironment in vivo, it is generally preferred that a disassociated cell culture derived from a biopsy tumor tissue includes similar types and ratios of various cells interacting with each other. Yet, the inventors also contemplate that in some embodiments, one type of cells can be preferably or dominantly cultured over other types of cells to obtain a more homogeneous group of cells from the biopsy tumor tissue. For example, the tumor cells from the biopsy tumor tissue can be isolated and/or selectively cultured via preferred culture technique for the tumor cell over other types of cells (e.g., sandwich culture, 3D culture, etc.) or depriving other cell types from the tissue (e.g., enzymatic degradation of stromal cells, etc.). The isolated and/or selectively cultured tumor cells can be further cultured to form an in vitro artificial tumor mass at least for 2 weeks, at least for 3 weeks, at least for 6 weeks, etc. as will be appreciated, separately cultivated cells can be rejoined (e.g., using same ratio as in tumor tissue) as desired.

The processed or unprocessed tumor tissue (from biopsy tissue) can then be analyzed using live cell interferometry to determine the activity of the immune cells in the tumor against the tumor cells and/or to identify immunogenic or immunologically active cells in the tumor microenvironment. As noted earlier, it was observed that immunologically active cytotoxic or cytolytic immune cells (e.g., active T cells, cytotoxic T cells, active NK cells, active NKT cells attacking cells upon recognition of the antigens or neoepitopes presented on the cells, etc.) increase their mass upon interacting with the cells presenting antigens or neoepitopes. Conversely, immunogenic cell (e.g., immune-sensitive tumor cells, tumor cells expressing antigens or neoepitopes) interacting with and being attacked by the immune cells (e.g., either cytolytic or cytotoxic attack, etc.) are likely to decrease their mass (e.g., due to apoptosis, necrosis, etc.). Therefore, viewed from a different perspective, decreased mass of the immune cells can be an indicator an of inactive or suppressed immune response or immune system in the tumor microenvironment, and an increased mass of tumor cells can be an indicative of proliferation of the tumor cells that overcome the immune response against the tumor cells in the tumor microenvironment.

Thus, in a preferred embodiment, at least one tumor cell and/or at least one immune cell can be selected from the tumor sample (e.g., acute slices, cultured slices, dissociated cells, unprocessed biopsy tissue) and the mass of those cells can be individually and/or collectively determined using the LCI. Preferably, the selected tumor cell and the immune cell are proximally located (e.g., within 100 μm, within 50 μm, within 25 μm, within 10 μm, etc.) such that the immune cell and the tumor cell can make a direct or indirect contact and/or interaction with each other, or at least the molecules secreted or presented by the immune cell (e.g., cytokines, etc.) can be transmitted to the tumor cells without a significant dilution. Thus, in this embodiment, the tumor cell and the immune cell that can be visibly distinguishable (e.g., by morphology, size, etc.) and located proximally with each other can be selected to measure the mass. Additionally, the mass of the tumor cell and the immune cell can be compared with other tumor cell and the immune cell, respectively in the same tissue examined under the LCI or the limited area of the tissue under the same field of view of the LCI.

It is especially preferred that the immune cells (especially immune competent cells) can be visually distinguishable from tumor cells or other types of the cells in the tumor tissue, and also from with each other such that not only type and numbers of immune competent cells in the tumor sample can be identified, but also their physiological status/activity and impact on tumor cells. Among other immune cells, especially contemplated immune competent cells include dendritic cells, CD4+ T cells, CD8+ T cells, cytotoxic T cells, NK cells, NKT cells, and M1 and M2 macrophages. Additionally, while some types of cells can be visually distinguished from other types of cells by their unique morphology, the inventors contemplate that tumor cells and/or various types of immune cells among heterogeneous cell populations in the tumor tissue can be visualized and detected by live labeling of the cells. Any suitable labeling methods that can label the cells without substantially interfering cell-cell interactions are contemplated. For example, some tumor cells and/or immune cells in the live tissue (or in the disassociated cell culture) can be labeled with a quantum dot coupled with a fluorescent dye (e.g., fluorescein isothiocyanate (FITC), etc.) and conjugated with peptide (e.g., single-chain variable fragment (scFv) or antibody fragment specific to a marker (e.g., antigens, receptor protein, etc.) of a type of cell, etc.).

Preferably, the immune status of the tumor can be determined from the mass of the tumor cell and/or the mass of the immune cells (and with that the anticipated immune response of the patient to a tumor, can be readily predicted by observing the cell mass of tumor cells and/or immune cells (e.g., immune competent cells) within a sample. The inventors contemplate that the standard (or threshold) for determining the immune status of the tumor may vary depending on the type of tumor, the patient's condition, and/or the patient's medical history. For example, the immune status of the tumor can be determined as immune-sensitive or "hot" if the tumor cell proximal to the immune cell shows the mass that is at least 10%, at least 20%, at least 30%, at least 40%, at least 50% less than other tumor cells, which do not proximally located to immune cells. For other example, the immune status of the tumor can be determined as immune-sensitive or "hot" if the immune cell proximal to the tumor cell shows the mass that is at least 10%, at least 20%, at least 30%, at least 40%, at least 50% more than other tumor cells, which do not proximally located to tumor cells. Conversely, the immune status of the tumor can be determined as immune-resistant or "cold" if the tumor cell proximal to the immune cell shows the mass that is substantially same or even at least 10%, at least 20%, at least 30%, at least 40%, at least 50% more than other tumor cells, which do not proximally located to tumor cells. For other example, the immune status of the tumor can be determined as immune-resistant or "cold", if the immune cell proximal to the tumor cell shows the mass that is substantially same or even at least 10%, at least 20%, at least 30%, at least 40%, at least 50% less than other tumor cells, which do not proximally located to tumor cells.

It is also contemplated that the immune status of the tumor can be determined by measuring collective or average mass of the tumor cells or immune cells in the tumor tissue and comparing with the average mass of non-tumor cells or immune cells, respectively, in the non-diseased tissue. For example, the mass of at least 20, at least 50, at least 100, or at least 300 tumor cells or immune cells in the tumor tissue, and the mass of substantially same number of non-tumor cells (or the same organ, for example, liver of healthy individual, noncancerous portion of the liver of the patient, etc.) can be measured under LCI, and the average mass of the tumor cells (or non-tumor cells) or immune cells can be calculated. The immune status of the tumor can be determined as immune-sensitive or "hot" if average mass of the tumor cell is at least 10%, at least 20%, at least 30%, at least 40%, at least 50% less than other similar-sized non-tumor cells (known to have similar size with average size of such type of tumor cells, etc.), or at least 10%, at least 20%, at least 30%, at least 40%, at least 50% less than other tumor cells present in different tumor mass in the same patient. Also, the immune status of the tumor can be determined as immune-sensitive or "hot" if average mass the immune cells in the sample is at least 10%, at least 20%, at least 30%, at least 40%, at least 50% more (larger) than the immune cells in the normal tissue (non-diseased tissue of the patient, or tissue from the healthy individual, etc.). Conversely, The immune status of the tumor can be determined as immune-resistant or "cold" if average mass of the tumor cell is substantially same or even at least 10%, at least 20%, at least 30%, at least 40%, at least 50% larger than other similar-sized non-tumor cells (known to have similar size with average size of such type of tumor cells, etc.), or at least 10%, at least 20%, at least 30%, at least 40%, at least 50% less than other tumor cells present in different tumor mass in the same patient. Also, the immune status of the tumor can be determined as immune-resistant or "cold" if average mass the immune cells in the sample is substantially same or even at least 10%, at least 20%, at least 30%, at least 40%, at least 50% less (smaller) than the immune cells in the normal tissue (non-diseased tissue of the patient, or tissue from the healthy individual, etc.).

The inventors contemplate that the behavior and/or interaction of the immune cell with the tumor cell in the tumor sample may not accurately reflect the in vivo behavior and/or interaction of the immune cell as the condition of biopsy and/or acute processing of the tumor tissue may differ from the in vivo condition (e.g., temperature, excessive cell stress from the invasive tissue excision, etc.). Thus, in some embodiments, the mass of the tumor cells and/or immune cells from the tumor sample can be determined over a period of time after the tumor tissue (or disassociated cells from the tumor cells) are placed on the ex vivo culture condition. Any suitable time windows and/or duration for analyzing cell mass in the tumor tissue are contemplated. For example, observation and analysis of cell mass under LCI can be performed in at least 1 hour, at least 3 hours, at least 6 hours, at least 12 hours, at least 24 hours, at least 3 days after the biopsy tissue was placed in the ex vivo culture condition (either processed or unprocessed). Once placed under LCI, the observation and analysis of cell mass of tumor cells and/or immune cells can be performed at least at least 1 hour, at least 3 hours, at least 6 hours, at least 12 hours continuously or periodically (e.g., every 5 min, every 10 min, every 30 min, every 1 hour, every 2 hours during the duration, etc.).

In some embodiments, where the LCI analysis is performed periodically on immune cells and/or tumor cells, it is contemplated that the tissues and/or cells can be placed under the LCI and the LCI is activated/operated periodically. For example, the LCI can be turned on (light on) to measure the cell mass every 1 min, every 5 min, every 10 min, every 30 min, every 1 hour, every 2 hours, while tissues and/or cells remains non-manipulated (e.g., not moved, untouched, etc.) during the measurements and in between the measurements. In other embodiments, the tissues and/or cells can be placed on the rotating/moving holder (e.g., tissue culture inserts), such that the tissues and/or cells can be placed directly under the light of LCI for every 1 min, every 5 min, every 10 min, every 30 min, every 1 hour, every 2 hours for a duration of measurement and moves away from the light. In such embodiments, it is preferred that a plurality of tissues and/or cells can be placed in a distinct location of the moving holder (e.g., multiple distinct tissue culture inserts on 6 well plate or petri dish, etc.) such that at least one or more tissues/cells can be measured and analyzed while the other tissues/cells are in between two measurements.

Additionally, the inventors contemplate that the efficacy of a treatment can be tested real-time on the tumor tissue/cells under LCI such that the efficacy of the treatment in vivo can be predicted. In some embodiments, the tumor sample (tissue or cells) can be treated with one or more treatment (e.g., antibodies, vaccines, checkpoint inhibitors, etc.), preferably after measuring the immune status of the tumor sample. For example, the tumor sample can be treated with one or more treatment (e.g., antibodies, vaccines, checkpoint inhibitors, etc.) and cell mass change of the tumor cell and/or immune cells can be measured real-time for a duration of time (e.g., at least 1 hour, at least 3 hours, at least 6 hours, etc.). The change of cell mass as a function of time (e.g., the shape of mass curve as a function of time if plotted on a graph, etc.) can provide a signature of the efficacy or metabolism of treatment. For example, for treatment A, the cell mass change may occur early (e.g., within 30 min) and be maintained for next 6 hours. For treatment B, the cell mass change may not occur until 6 hours after the treatment. Based on such signature, the efficacy and metabolism of the treatment can be similarly predicted in vivo such that the treatment options can be modulated and selected.

Further, measurement of cell mass can be used to measure or predict the metastasis rate. Some tumor cells that are undergoing metastasis often have altered cytoskeletal properties, in particular to be more deformable and contractile. Thus, in one embodiment, the change of a plurality of tumor cells in the tumor sample can be measured such that information of the ratio of the deformed cells in the tumor sample and/or the degree of deformation as a function of time can be obtained. From at least one of the ratio of the deformed cells in the tumor sample and/or the degree of deformation as a function of time, the metastasis rate of the tumor cells in the tumor sample can be measured and the metastasis rate of tumor cells of the tumor in vivo can be predicted.

Alternatively, the inventors also contemplate that tumor cell-immune cell interaction conditions can be artificially made with more homogeneous cell populations by using the artificial tumor mass generated from the tumor cells of the tumor tissue sample. In one embodiment, various types of endogenous, naive immune cells from the tumor tissue sample (or circulating cells, or cells from a lymph node) can be isolated and separated by cell types (e.g., CD4+ T cells, CD8+ T cells, B cells, by Fluorescence-activated cell sorting (FACS) or using antibodies specific to a marker of specific immune cells (V$\alpha$24-J$\alpha$18 for human NKT cells, etc.), etc.). In addition, it is also contemplated that some immune cells can be isolated from the tumor tissue and can be further expanded ex vivo to increase the number of the cells for further experiments and analysis. For example, NK cells or NKT cells can be placed in a cell culture media (e.g., AIMV® medium, RPMI1640® etc.) that includes one or more activating conditions. The activating conditions may include addition of any molecules that can stimulate NK or NKT growth, induce cell division of NK or NKT, and/or stimulate cytokine release from NK or NKT that can further expand NK or NKT. It is contemplated that the activating conditions may vary depending on the timing of the ex vivo expansion and activation.

For example, NK cell expansion can be performed using various activating molecules added in the culture media including cytokines (e.g., IL-2, IL-15, etc.), monoclonal antibodies (e.g., murine monoclonal antibody against CD3 (OKT3TM), etc.), or using cell-to-cell interaction with activating cells (e.g., K562 cells, a cell line derived from a patient with myeloid blast crisis of chronic myelogenous leukemia and bearing the BCR-ABL1 translocation, etc.)

With respect to NKT cells, ex vivo expansion and activation of NKT cells can be performed using the activator of endogenous NKT T cell receptor or antibodies against the components of the endogenous NKT T cell receptor, before the endogenous NKT T cells are removed by knock-in of recombinant nucleic acid. However, after the endogenous NKT T cells are removed by knock-in of recombinant nucleic acid, it is contemplated that the activator of endogenous NKT T cell receptor or antibodies against the components of the endogenous NKT T cell receptor may not be used for effective ex vivo expansion and activation.

Thus, the activating molecules may include T cell receptor antibodies (e.g., anti-CD2, anti-CD3, anti-CD28, $\alpha$-TCR-V $\alpha$24+ antibodies, preferably immobilized on beads, etc.), a glycolipid (e.g., $\alpha$-GlcCer, $\alpha$-ManCer, GD3, etc.), a glycolipid coupled with CD1 (e.g., CD1d, etc.) if the ex vivo expansion and activation is performed before the recombinant nucleic acid is introduced into the NKT cells. After the recombinant nucleic acid is introduced into the NKT cells, the activating molecules may include one or more cytokines (e.g., IL-2, IL-5, IL-7, IL-8, IL-12, IL-12, IL-15, IL-18, and IL-21, preferably human recombinant IL-2, IL-5, IL-7, IL-8, IL-12, IL-12, IL-15, IL-18, and IL-21, etc.) in any desirable concentration (e.g., at least 10 U/ml, at least 50 U/ml, at least 100 U/ml), etc. In some embodiments, the activation conditions may include culturing the isolated and enriched NKT cells with autologous or allogeneic peripheral blood mononuclear cells (PBMC) feeder cells.

The isolated immune cells can further be placed close to the artificial tumor (e.g., in the same culture dish, within less than 5 cm distance, less than 3 cm distances, less than 1 cm distance, less than 0.5 cm distance, etc.), and co-incubate with the artificial tumor mass for at least 3 hours, at least 6 hours, at least 12 hours, at least 24 hours, at least 3 days such that the immune cells can infiltrate the artificial tumor mass and elicit the immune response against the tumor cells. In some embodiments, a plurality of artificial tumor mass can be generated from a single biopsy tumor tissue, and each of the artificial tumor mass can be contacted with different types of isolated immune cells (CD4+ T cells, CD8+ T cells, NK cells, NKT cells, macrophage, etc.) or a combination of isolated immune cells (e.g., at least two of immune competent cells in a ratio of at least 1:1, at least 1:2, at least 1:3, at least 1:5, etc.).

In some embodiment, the tumor samples (acute slice, cultured slice, disassociated cells, derived from the biopsy tumor tissue) and/or artificial tumor can be contacted (or at least co-placed with) genetically modified or genetically engineered immune cells. For example, the artificial tumor can be contacted NK92 cells and derivatives thereof (e.g., aNK cells, haNK cells, taNK cells, all commercially available from NantKwest, 9920 Jefferson Blvd. Culver City, CA 90232). For other example, the tumor samples and/or the artificial tumor can be contacted genetically engineered T cells, NK cells, or NKT cells expressing a recombinant chimeric antigenic receptor (CAR) that specifically bind tumor antigen or neoepitope expressed by the tumor cells in the biopsy tumor tissue. For still other example, the tumor samples and/or the artificial tumor can be contacted ex vivo activated cytotoxic immune cells (e.g., ex vivo expanded and/or activated NK cells or NKT cells with cytokines, etc.). With that, the inventors contemplate that the immune status of the tumor to the cancer vaccine or modified immune cells can be determined such that the anticipated effect of the cancer vaccine or modified immune cells against the tumor cells can be predicted. In such example, it is preferred that the tumor-associated antigens or neoepitopes that are tumor-specific and/or patient-specific are identified and one or more nucleic acid constructs encoding CAR specific to those tumor-associated antigens or neoepitopes. Typically, the tumor associated antigens and/or neoepitopes (which are typically patient-specific and tumor-specific) can be identified from the omics data obtained from the cancer tissue of the patient or normal tissue (of the patient or a healthy individual), respectively. Omics data typically includes information related to genomics, transcriptomics, and proteomics.

The artificial tumor mass contacted (or at least co-placed with) the isolated immune cells and the artificial tumor mass uncontacted the isolated immune cells then can be further observed to determine the cell mass of the tumor cells and immune cells in the tumor mass. In such embodiment, the immune status of the tumor cells in the tumor (as reflected in artificial tumor mass) can be determined as immune-sensitive or "hot" if average mass of the tumor cell in the artificial tumor contacting the immune cells is at least 10%, at least 20%, at least 30%, at least 40%, at least 50% less than average mass of the tumor cell in the artificial tumor without contacting the immune cells. Also, the immune status of the tumor can be determined as immune-sensitive or "hot" if average mass the immune cells in the artificial tumor contacting the immune cells is at least 10%, at least 20%, at least 30%, at least 40%, at least 50% more (larger) than the immune cells before or without contacting the artificial tumor mass. Conversely, the immune status of the tumor cells in the tumor (as reflected in artificial tumor mass) can be determined as immune-resistant or "cold" if average mass of the tumor cell in the artificial tumor contacting the immune cells is substantially same or even at least 10%, at least 20%, at least 30%, at least 40%, at least 50% larger (more) than average mass of the tumor cell in the artificial tumor without contacting the immune cells. Also, the immune status of the tumor can be determined as immune-resistant or "cold" if average mass the immune cells in the artificial tumor contacting the immune cells is substantially same or even at least 10%, at least 20%, at least 30%, at least 40%, at least 50% less (smaller) than the immune cells before or without contacting the artificial tumor mass.

Additionally, the inventors contemplate that the immune status of the tumor can be determined by considering other information on the tumor cells and/or immune cells in addition to the cell mass of the tumor cell or the immune cell. In one embodiment, ratios among different types of immune cells in an area of the tumor tissue (e.g., per 1 mm$^2$, per 10 mm$^2$, per 100 mm$^2$, etc.) can be determined and used as an indicator of the immune status as one or more different types of immune competent cells may serve as a proxy indicator for immunogenicity of the tumor. For example, where the tumor is infiltrated with M2 macrophages and is relatively poor in NK cells and CD8+ T cells, the tumor of the patient may be deemed immunologically "cold". On the other hand, where the tumor is relatively rich in CD4+/CD8+ T cells and NK cells, the tumor of the patient may be immunologically "hot".

In another embodiment, the morphologies (e.g., shape, height, etc.) of the tumor cells and/or immune cells (of the same type), degree of cell to cell adhesion, or cell-extracellular matrix adhesion of the tumor cells and/or immune cells, or relative locations of tumor cells and immune cells in the tumor tissue can be observed and analyzed to derive immune status information. For example, where the immune cells, especially cytotoxic immune cells, in the tumor tissue are not located in vicinity of the tumor cells, such relative location information may indicate that the tumor may be deemed immunologically "cold" either by prohibiting the infiltration of the cytotoxic immune cells to the tumor to have a contact to the tumor cells or by actively removing the infiltrated cytotoxic immune cells from the tumor microenvironment.

Some immunologically "cold" tumor may be induced to be at least immunologically neutral or even "hot" if the tumor microenvironment is optimized. Thus, inventors further contemplate that the tumor sample determined to be "cold" can be further treated with one or more co-stimulatory molecules, an immune stimulatory cytokine, and/or a protein that interferes with or down-regulates checkpoint inhibition. In some embodiments, can be analyzed under LCI and upon determination of its immune status as "cold", the tumor sample can be treated with one or more co-stimulatory molecules, an immune stimulatory cytokine, and/or a protein that interferes with or down-regulates checkpoint inhibition for at least 1 hour, at least 6 hours, at least 12 hours, at least 24 hours, at least 3 days, at least 7 days before determining the cell mass of tumor cells and/or immune cells under LCI again. In other embodiments, the tumor sample can be divided into at least two badges (e.g., two acute slices, two separate cell cultures from the same biopsy tumor tissue, maintained in the same condition, etc.). In these embodiments, one batch of the tumor sample can be used without treatment to determine the mass of tumor cells and/or immune cells, and another badge of the tumor sample can be used after treatment with co-stimulatory molecules or their ligands, an immune stimulatory cytokine, and/or a protein that interferes with or down-regulates checkpoint inhibition to determine the mass of tumor cells and/or immune cells.

Suitable co-stimulatory molecules include, but not limited to, CD80, CD86, CD30, CD40, CD30L, CD40L, ICOS-L, B7-H3, B7-H4, CD70, OX40L, 4-1BBL, while other stimulatory molecules with less defined (or understood) mechanism of action include GITR-L, TIM-3, TIM-4, CD48, CD58, TL1A, ICAM-1, LFA3, and members of the SLAM family. In addition, any suitable types of cytokines to boost the immune response are contemplated. Especially preferred cytokines and cytokine analogs include IL-2, IL-15, and IL-15 superagonist (ALT-803), IL-21, IPS1, and LMP1.

With respect to a protein that interferes with or down-regulates checkpoint inhibition, it is contemplated any suitable peptide ligands that bind to a checkpoint receptor are contemplated. Most typically, binding will inhibit or at least reduce signaling via the receptor, and particularly contemplated receptors include CTLA-4 (especially for CD8$^+$ cells), PD-1 (especially for CD4$^+$ cells), TIM1 receptor, 2B4, and CD160. For example, suitable peptide binders can include antibody fragments and especially scFv, but also small molecule peptide ligands (e.g., isolated via RNA display or phage panning) that specifically bind to the receptors (e.g., ipilimumab, nivolumab, etc.).

In addition, it is contemplated that where the tumor sample determined to be "cold", some "cold" tumor samples may be transformed to "hot" by treating the tumor cells with stress molecules that can induce the tumor cells to be immunogenic. For example, tumor cells can be treated with a continuous exposure or metronomic exposure (e.g., using one or more chemotherapeutic drugs at relatively low dose) or other stress conditions such as hypoxia, local heat shock treatment (e.g., at 42 degree celcius for 1 min, for 3 min, for 5 min, etc.), exposure to toxins and/or mechanical damage (e.g., partial surgical removal of cancer tissue, etc.). In such embodiment, responsiveness of a tumor (reflected by changes in mass of tumor cells or immune cells) may be evaluated over multiple LCI measurements to identify the optimal stress conditions to convert the immune status of the tumor.

Moreover, it is contemplated that where the tumor sample determined to be "cold", the "cold" tumor samples may be transformed to "hot" by inducing a condition in the tumor to attract more immune competent cells. For example, the tumor tissue may be pre-treated with chemokines that may be effective in chemo-attraction of immune competent cells, and especially CD8+ and CD4+ T cells, for at least 30 min, at least 1 hour, at least 3 hours, at least 6 hours, at least 12 hours before re-evaluating responsiveness of a tumor (reflected by changes in mass of tumor cells or immune cells) over multiple LCI measurements.

The inventors contemplate that the immune response against tumor by patient's own immune system or boosted by immunotherapy can be predicted based on the determined immune status. As used herein, the immune response that is predicted based on the immune status refers a effectiveness or responsiveness of a given immunotherapy against the tumor or a likelihood of success of the immunotherapy against the tumor (e.g., by decreasing the tumor size at least 20%, at least 30%, at least 40%, at least 50%, etc., by suppressing the metastasis of the tumor, etc.). Without wishing to be bound to any specific theory, the immunologically "hot" tumors are more likely to respond to individualized immunotherapy (e.g., personalized cancer vaccine, etc.) such that the individualized immunotherapy or other types of immunotherapy can be highly recommended as a treatment option against the tumor. Conversely, when the tumor is determined to be immunologically "cold", those tumors are less likely to respond to individualized immunotherapy (e.g., personalized cancer vaccine, etc.) such that the individualized immunotherapy or other types of immunotherapy may not be the first prioritized option to treat the tumor. In this case, some additional or other types of treatment options can be provided. For example, where the tumor determined to be immunologically "cold", yet the tumor is conditionally "hot" when the immune stimulatory molecule is pre-treated, the treatment option for co-treatment or sequential treatment of one of more immune stimulatory molecules with personalized cancer vaccine can be recommended.

The inventors further contemplate that the metastasis rate or possibility of metastasis originated from the tumor can be predicted based on the determined immune status. Without wishing to be bound to any specific theory, the immunologically "hot" tumors are less likely to metastasize to other part of the body such that metastasis rate or possibility of metastasis from the tumor is relatively low. Conversely, when the tumor is determined to be immunologically "cold", those tumors are more likely to metastasize to other part of the body such that metastasis rate or possibility of metastasis from the tumor is relatively high.

Optionally, the tumor tissue and/or sample that was used to evaluate the immune status of the tumor or the tumor tissues can be further placed for additional molecular and cellular analysis. For example, where the tumor tissue is obtained from one of the metastasized tumors and the tumor tissue is determined immunologically hot or cold, omics data can be obtained from the tumor cells in the tumor tissue to identify any key molecules and/or mutations that contributes the immune status of the tumor tissue. In some embodiments, a tumor cell that showed response or nonresponse to the immune cell under LCI can be picked up using a micropipette and the genetic materials (e.g., DNA, RNA, etc.) can be retrieved from the single tumor cell. In those embodiments, the molecular analysis and omics data analysis can be performed in a single-cell level.

For other example, the tumor tissue and/or sample that was used to evaluate the immune status of the tumor or the tumor tissues can be further processed (e.g., freezing, fixing with formalin-fixed paraffin-embedded (FFPE) technique, fixing with paraformaldehyde (PFA), etc.) so that the tissue can be analyzed using immunohistochemical assays or biochemical assays (e.g., western blotting, northern blotting, etc.) to determine the cell types (e.g., using cell-specific markers, etc.), distribution of different types of cells in the tumor tissue relative to the tumor cells (e.g., location and accumulation of MDSC, Treg, proximity of different types of immune cells to the tumor cells, etc.), or cellular and molecular changes of the immune cells and/or tumor cells (e.g., expression level of receptors in different types of immune cells, heterogeneity of tumor cells, etc.) in the immunologically hot or cold tumor tissues.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise. Unless the context dictates the contrary, all ranges set forth herein should be interpreted as being inclusive of their endpoints, and open-ended ranges should be interpreted to include commercially practical values. Similarly, all lists of values should be considered as inclusive of intermediate values unless the context indicates the contrary.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. An immunotherapeutic method of treating a patient having a tumor, comprising:
   obtaining, prior to an immunotherapeutic treatment, a tumor sample from the patient;
   measuring a collective or average mass of tumor cells and a collective or average mass of immune competent cells in the tumor sample by using live cell interferometry;
   determining an immune status of the tumor sample as hot when the collective or average mass of tumor cells proximal to an immune competent cell is at least 20% less than other tumor cells which are not proximally located to immune competent cells, or when the collective or average mass of immune competent cells proximal to tumor cells is at least 20% larger than other immune competent cells which are not proximally located to tumor cells, wherein the term proximal or proximally refers to within 100 μm; and
   administering, upon determining the immune status as hot, the immunotherapeutic treatment to the patient.

2. The method of claim 1, further comprising a step of identifying a type of the immune competent cell.

3. The method of claim 1, wherein the measuring a collective or average mass of the tumor cells and the immune competent cells comprises measuring changes in collective or average mass over a period of time.

4. The method of claim 1, further comprising contacting the tumor sample with an immune stimulatory cytokine, a checkpoint inhibitor, or an immunotherapeutic agent.

5. The method of claim 4, further comprising comparing the at least one of a mass of a tumor cell and a mass of an immune competent cell before and after contacting the tumor sample with the immunotherapeutic agent.

6. The method of claim 1, wherein the tumor sample is a portion of an artificial tumor that is generated from a tumor biopsy of the patient.

7. The method of claim 1, wherein the immune competent cell is labeled with a marker.

8. The method of claim 1, wherein the mass of the tumor cell is determined by comparing optical thickness of the tumor cell and optical thickness of a control cell.

9. The method of claim 1, further comprising fixing the tumor cell and the immune competent cell in the tumor sample and identifying a type of at least one of the tumor cell and the immune competent cell by labeling with a marker.

10. The method of claim 1, wherein the tumor cell and the immune competent cell are each disassociated and placed in cell culture medium.

11. The method of claim 1, wherein the tumor cell and the immune competent cell are in acutely sliced tissue.

12. The method of claim 1, wherein the tumor cell and the immune competent cell are in cultured sliced tissue.

13. The method of claim 1, further comprising identifying presence of a neoepitope on the tumor cell, wherein the neoepitope is specific for the patient and the tumor.

* * * * *